United States Patent [19]

Knudsen et al.

[11] Patent Number: 4,928,254

[45] Date of Patent: May 22, 1990

[54] LASER FLASH THERMAL CONDUCTIVITY APPARATUS AND METHOD

[76] Inventors: Arne K. Knudsen, 4007 Oak Ct.; Scott H. Delzer, 5316 Russell St.; Charles A. Langhoff, 1601 Clover La., all of Midland, Mich. 48640

[21] Appl. No.: 187,372

[22] Filed: Apr. 28, 1988

[51] Int. Cl.$^5$ .................. G06F 15/20; G01N 25/20
[52] U.S. Cl. .................. 364/556; 250/341; 364/550; 374/10; 374/43; 374/44
[58] Field of Search .................. 374/9, 10, 29, 43, 44; 364/477, 550, 556, 557; 250/338.1, 341

[56] References Cited

U.S. PATENT DOCUMENTS

| | | | |
|---|---|---|---|
| 4,232,543 | 11/1980 | Eguchi et al. | 374/44 |
| 4,283,935 | 8/1981 | Eguchi et al. | 374/44 |
| 4,568,198 | 2/1986 | Szabó et al. | 374/43 |
| 4,630,938 | 12/1986 | Piorkowska-Palczewska | 374/29 |

OTHER PUBLICATIONS

Fyzikolny Casopis (1970), No. 1; "Measurement of Thermal Conductivity of Thin Samples of a Finite Length"; J. Kristofic et al., pp. 48-55.

W. J. Parker et al., "Flash Method of Determining Thermal Diffusivity, Heat Capacity, and Thermal Conductivity*," *Journal of Applied Physics*, vol. 32, No. 9, Sep. 1961, pp. 1679-1684.

L. Pawlowski et al., "The Least Square Method in the Determination of Thermal Diffusivity Using a Flash Method," *Revue De Physique Appliquee*, vol. 21, No. 2, Feb. 1986, pp. 83-86.

A. Chmielewski et al., "Computerized Data Acquisition and Analysis For Measuring Thermal Diffusivity" Society of Automotive Engineers, Inc. No. 859462 1985, pp. 3.565-3.568.

"Standard Test Method For Thermal Diffusivity of Carbon and Graphite by a Thermal Pulse Method" The American Society for Testing and Materials Designation C714, Aug. 1972.

Yutaka Tada et al., "Laser Flash Method For Measuring Thermal Conductivity Of Liquids—Application To Low Thermal Conductivity Liquids," *Rev. Sci. Instrum.* vol. 29, No. 9, Sep. 1978, pp. 1305-1314.

Martin I. Darby, "Analysis of Thermal Conductivity Experiments on Glass at High Temperatures," *High Temperatures—High Pressures*, vol. 15, 1983, pp. 629-644.

Andrew Whittaker et al., "Thermal Diffusivity of Some Fine-Weave Carbon/Carbon-Fibre Composites," *High Temperatures—High Pressures*, vol. 17, 1985, pp. 225-231.

L. M. Clark III and R. E. Taylor, *Journal of Applied Physics*, vol. 46, No. 2, 2/1975, pp. 714-719.

H. L. Lee et al., "Comparison of Data For Thermal Diffusivity Obtained by Laser-Flash Method Using Thermocouple and Photodetector," *J. Am. Ceram. Soc.*, vol. 68, No. 1, C-12-C-13, Jan. 1985.

F. Righini et al., "Pulse Method of Thermal Diffusivity Measurements (A Review)," *High Temperatures—High Pressures*, vol. 5, 1973, pp. 481-501.

Y. Takahashi, "Measurement of Thermophysical Properties of Metals and Ceramics By the Laser-Flash Method," *International Journal of Thermophysics*, vol. 5, No. 1, Feb. 8, 1984, pp. 41-52.

(List continued on next page.)

Primary Examiner—Kevin J. Teska
Attorney, Agent, or Firm—Harness, Dickey & Pierce

[57] ABSTRACT

A sequence of temporally-spaced radiant energy pulses are applied to the front surface of the sample and the heat rise caused by each thermal pulse is measured at the second surface using a suitable thermocouple or infrared sensor. The temperature rise data for each pulse is digitized and stored in a two-state memory device such as a random access memory. The data from each successive pulse is coadded and statistically processed by averaging to derive a set of favored values indicative of the temperature of the sample as a function of time. The favored values data is further processed using a least squares curve fitting algorithm to determine a numerical value indicative of the diffusivity of the sample.

8 Claims, 3 Drawing Sheets

OTHER PUBLICATIONS

M. A. Bucknam et al., "The Measurement of the Thermal Conductivity of Refractories By The Laser-Flash Method," *Transactions of the British Ceramic Society*, vol. 82, No. 1, 1983, pp. 18-23.

D. L. Balageas, "Nouvelle Methode D'interpretation des Thermogrammes Pour la Determination de la Diffusivite Thermique par la Methode Impulsionnelle," *Revue Phys. Appl.*, vol. 17, Apr. 1982, pp. 227-237.

R. E. Taylor et al., "Thermal Diffusivity of Fiber-Reinforced Composites Using The Laser Flash Techinque," *Carbon*, vol. 23, No. 2, 1985, pp. 215-222.

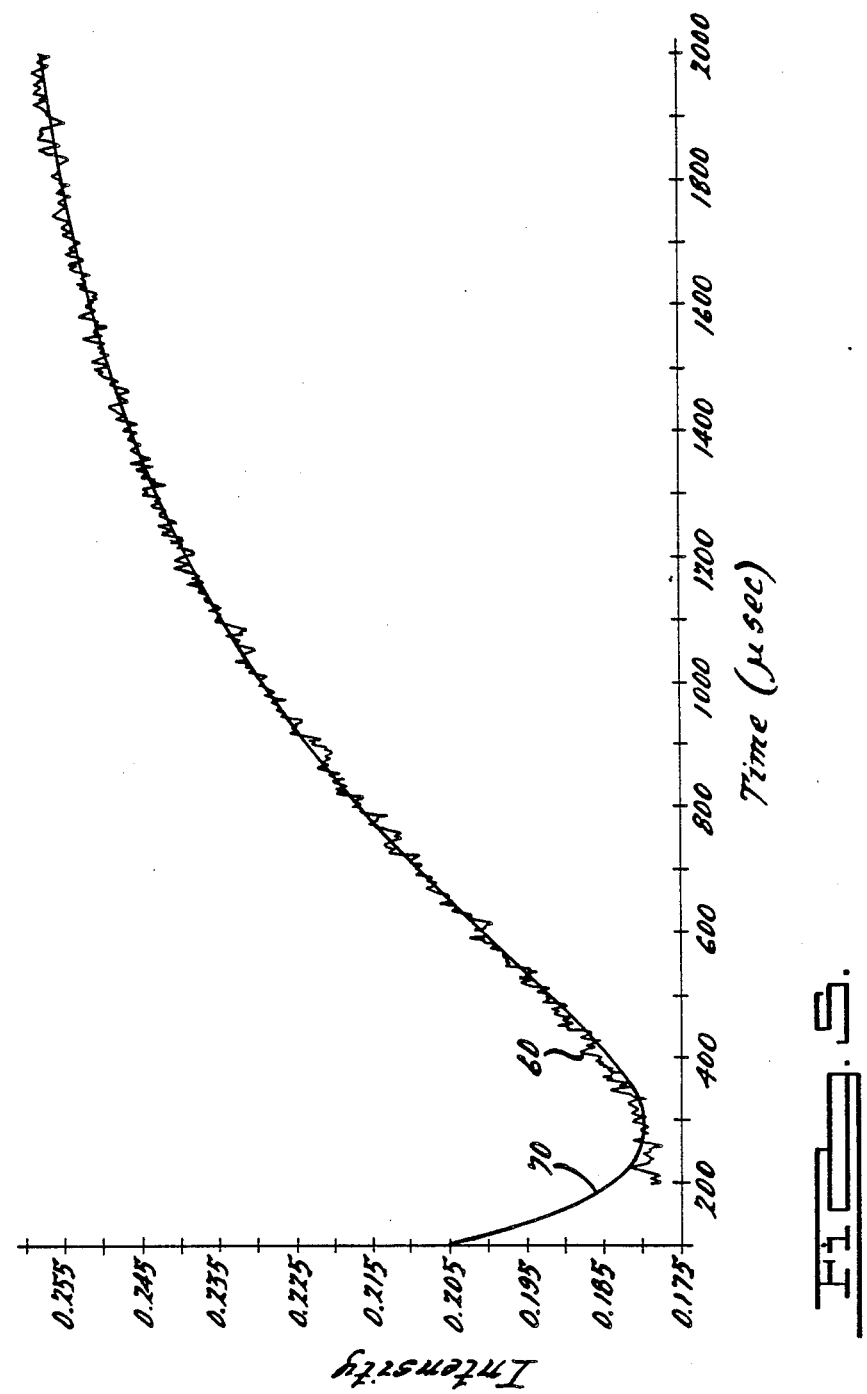

LASER FLASH THERMAL CONDUCTIVITY APPARATUS AND METHOD

BACKGROUND AND SUMMARY OF THE INVENTION

The present invention relates generally to thermal diffusivity measurement using laser flash techniques. More particularly, the invention relates to an improved laser flash apparatus and method which provides high accuracy at comparatively low laser power levels, so that the sample under test, and any coating applied thereto, are not appreciably degraded or damaged during the test.

In many industries, particularly in the materials industries, there is a need to accurately measure thermal diffusivity. In the semiconductor industry, for example, thermal diffusivity is an important factor in designing new substrate materials to conduct heat away from electronic components. Ceramic materials are becoming increasingly popular in this application, since these materials can demonstrate comparatively high thermal conductivity with comparatively low electrical conductivity. In developing new ceramic materials with high thermal conductivity the ability to quickly and accurately measure thermal diffusivity is quite important. With accurate and conveniently obtainable diffusivity data the ceramic engineer or scientist can more readily experiment with new formulations and fine-tune existing formulations for optimal thermal conductivity.

The flash method described by Parker in "Flash Method of Determining Thermal Diffusivity, Heat Capacity, and Thermal Conductivity," *Journal of Applied Physics*, 32(8), pages 1679–1684 (1961), W. J. Parker, R. J. Jenkins, C. P. Butler and G. L. Abbott, remains the most commonly used technique for measuring thermal diffusivity.

Briefly, the Parker method employs a thermal pulse source in the form of a flash tube (lasers are commonly used today) to apply a thermal pulse to one surface or portion of the sample under test. The thermal pulse propagates through the sample, manifesting itself as a temperature variation in the sample over time. A temperature sensor, such as a thermocouple contact sensor or an infrared noncontact sensor, senses a temperature rise on the rear surface or portion of the sample, which is indicative of the thermal diffusivity of the sample. The sensor output is fed to an oscilliscope to which a camera is attached for photographing the oscilliscope waveform. The waveform represents the temperature variation as a function of time. Diffusivity is then calculated based on the one-half time ($t_{\frac{1}{2}}$), that is, the time taken for the temperature to rise halfway between the ambient starting temperature and the final temperature, as revealed in the photograph of the oscilloscope waveform. The relationship between one-half time and diffusivity may be expressed by the following equation:

$$\alpha = \frac{0.139L^2}{t_{\frac{1}{2}}}; \tag{1}$$

where $\alpha$ is the diffusivity and L is the sample thickness.

Thermal conductivity (K) is the product is diffusivity ($\alpha$), the density ($\rho$) and the heat capacity ($C_p$):

$$K = \alpha C_p \rho \tag{2}$$

In implementing the Parker flash method care must be taken to prevent the initial heat pulse of the radiant energy source from directly illuminating the sensor, since this could alter the ability of the sensor to accurately respond to the temperature rise as it diffuses or propagates through the sample. With completely opaque samples careful masking is generally sufficient to prevent direct sensor illumination. However, translucent or transparent materials present a problem. Direct optical illumination of the sensor through the sample can disturb the sensor reading and obfuscate the relevant temperature rise data.

One proposed solution has been to coat the translucent or transparent sample with an opaque material. Another solution has been to restrict testing to samples of sufficient thickness such that optical transmission through the sample is greatly attenuated. Both of these approaches have been far from satisfactory.

Ceramic substrates of the type presently used in the semiconductor industry are comparatively thin (on the order of 25 to 40/1000ths of an inch) and are often not fully opaque at these thicknesses. Optical transmission through these samples is problematic and can adversely affect the sensor and alter or disturb the diffusivity data. Providing the ceramic substrate with a coating of opaque material will, of course, prevent optical transmission from interfering with the sensor, although there has been a considerable problem with the laser energy destroying the coating and thereby exposing the sensor to unwanted illumination.

Attempts at lowering the power of the laser have not heretofore been successful since lowering the laser power also lowers the heat pulse signal relative to the noise level of the measurement system. In addition, most attempts at lowering the laser power have involved lowering the laser power supply excitation, which changes the pulse shape of the laser and adversely affects the accuracy of the measurement.

The present invention overcomes the coating destruction problem by advantageously utilizing a low power laser as a radiant energy heat pulse source. The laser employed in the presently preferred embodiment develops an output heat pulse on the order of 0.7 joules, in contrast with the significantly higher powered lasers used in conventional flash methods. For example, Parker used a flash tube dissipating 400 joules of energy in each flash. A more recent publication described a modified Parker technique using a ruby laser producing 3 joules of energy. See Yutaka Tada et al., "Laser Flash Method for Measuring Thermal Conductivity of Liquids-Application to Low Thermal Conductivity Liquids," *Rev. Sci. Instrum.*, Vol. 49, No. 9, pp. 1305–1313, September 1978.

The present invention is able to use inexpensive and nondestructive low power laser sources by means of a sophisticated signal processing technique whereby a plurality of temporally spaced low power radiant energy pulses are applied to a first portion (e.g. front surface) of the sample, each pulse causing a temperature rise to propagate through the sample to a second portion (e.g. rear surface). The temperature rise associated with each pulse is individually sensed, preferably using a noncontact infrared sensor, and electrically recorded as data in a two-state memory device such as the random access memory of a computer. The data is then statistically processed to derive a set of favored values indicative of the temperature of the second portion of the sample as a function of time. Preferably the statistical processing includes signal averaging of the sensed data.

In the presently preferred embodiment approximately 1000 data samples are taken during the relevant time period which is a function of the rise time of the thermal signal (from the onset of the thermal pulse until approximately three to four $t_{\frac{1}{2}}$ times thereafter) for each pulse. A plurality of single shot pulses are applied to the sample in succession and the data acquired after each pulse is coded and averaged. Although the thermal pulse signal power at a 0.7 joule output is quite low, the received signal at the sensor is greatly enhanced by the statistical processing. This results from the fact that random signals and noise in the measurement system tends to cancel out when averaged over a number of iterations, whereas the signal of interest resulting from the heat pulse propagation tends to add constructively with successive iterations. Thus the statistical processing greatly improves the signal-to-noise ratio and allows the acquisition of good thermal data using the low power heat source.

The statistically processed data, representing a set of favored values indicative of the temperature of the second surface or portion as a function of time, is then further processed to determine the diffusivity of the sample. In the presently preferred embodiment a least squares curve-fitting algorithm is applied to the favored values data and the curve fit is optimized to the data by adjusting numerical parameters indicative of the thermal diffusivity. In the preferred embodiment the least squares curve fit algorithm is used based on the a priori assumption that the data will fit a curve defined by the following equation representing sensor reading as a function of time with diffusivity being an adjustable parameter:

$$f(x) = c + b(1 - 2\exp(-ax) + 2\exp(-4ax)) \tag{3}$$

where (c) is the baseline of the curve, (b) is the amplitude of the curve and (a) is directly related to the diffusivity ($\alpha$) by the equation:

$$\alpha = a(L/\pi) \tag{4}$$

The curve-fitting algorithm as well as the statistical processing may be performed by a digital computer with the diffusivity parameter ($\alpha$) yielding the desired numerical end result.

For a more complete understanding of the invention, its objects and advantages, refer to the following specification and to the accompanying drawings.

BRIEF DESCRIPTION OF THE DRAWINGS

FIG. 5 is a graph of sensor output intensity as a function of time, illustrating the data after statistical processing to yield a set of favored values and also illustrating the curve fit selected by the invention for the illustrated data from which the diffusivity may be determined.

DESCRIPTION OF THE PREFERRED EMBODIMENT

Figure 1:
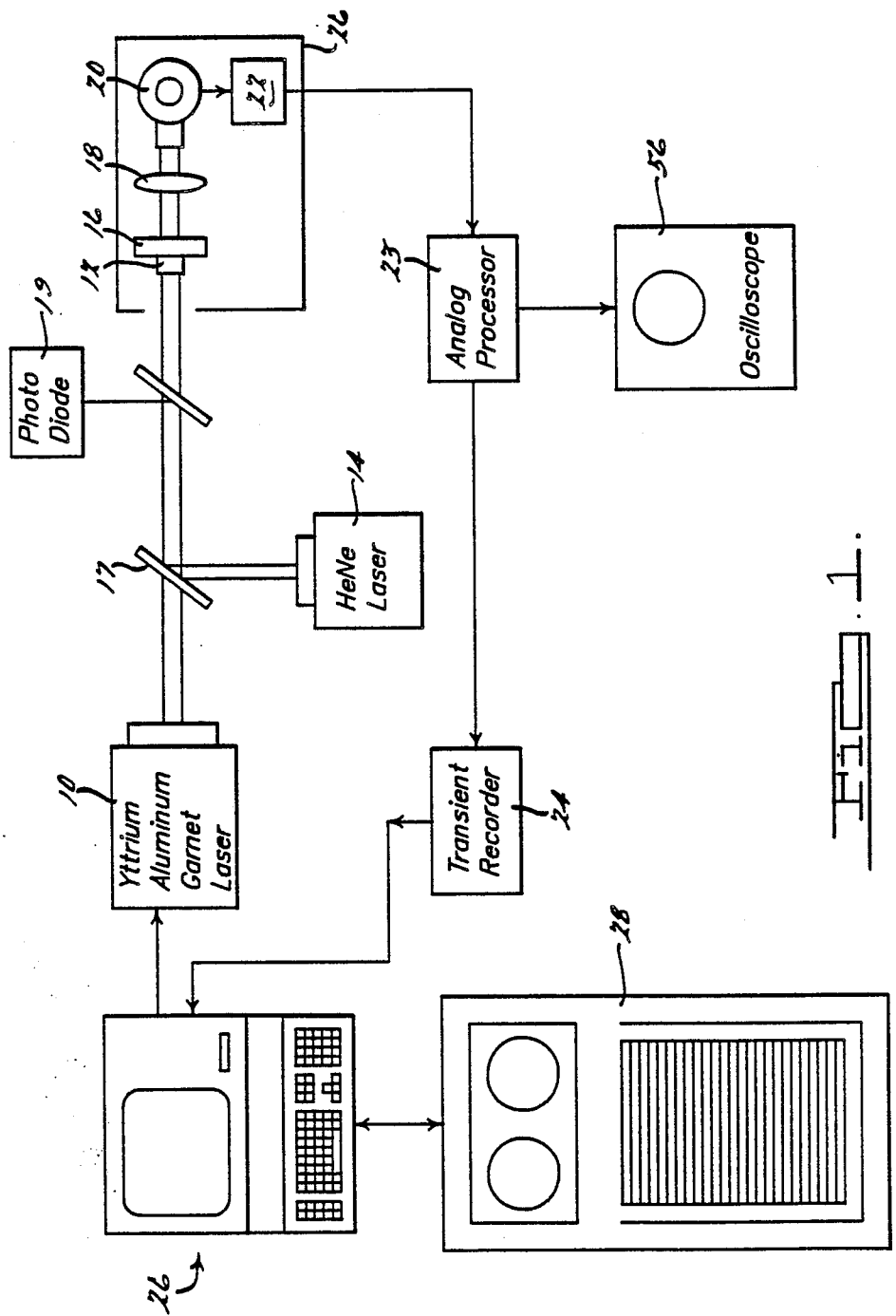
FIG. 1 is a schematic block diagram of the presently preferred embodiment of the laser flash apparatus, also useful in understanding the method of the invention.

The presently preferred laser flash apparatus is illustrated in FIG. 1. A yttrium aluminum garnet (YAG) laser 10 delivers a pulsed thermal energy signal to sample 12. Laser 10 has an output at a wavelength of 1.06 microns of approximately 0.7 to 1.0 joules per pulse. A suitable laser for this purpose is the Quantel Model YG400. The presently preferred laser 10 has two modes of operation, a higher power Q-switched mode which delivers approximately 1.0 joules per pulse and a non-Q-switched mode which delivers about 0.7 to 0.85 joules per pulse. An optional visible light HeNe laser 14 provides a beam colinear with the invisible YAG laser beam via mirror 17 to aid in sample alignment if desired. A photodiode 19 sampling in front of the sample 12 may be used if desired to provide a feedback signal to microcomputer 26 if desired.

A typical sample 12 may be a thin (less than 2 mm) disk which is opaque to both the YAG laser and to the plasma generated on the surface of the sample, provided with suitable opaque coating if necessary. The sample is fixed in a holder such as 1.125 inch inner diameter aluminum cylinder sample holder 16. Graphite apertures, are placed immediately in front of and behind the sample to prevent any stray laser light and plasma generated light from reaching the detector or sensor 20.

Figure 2:
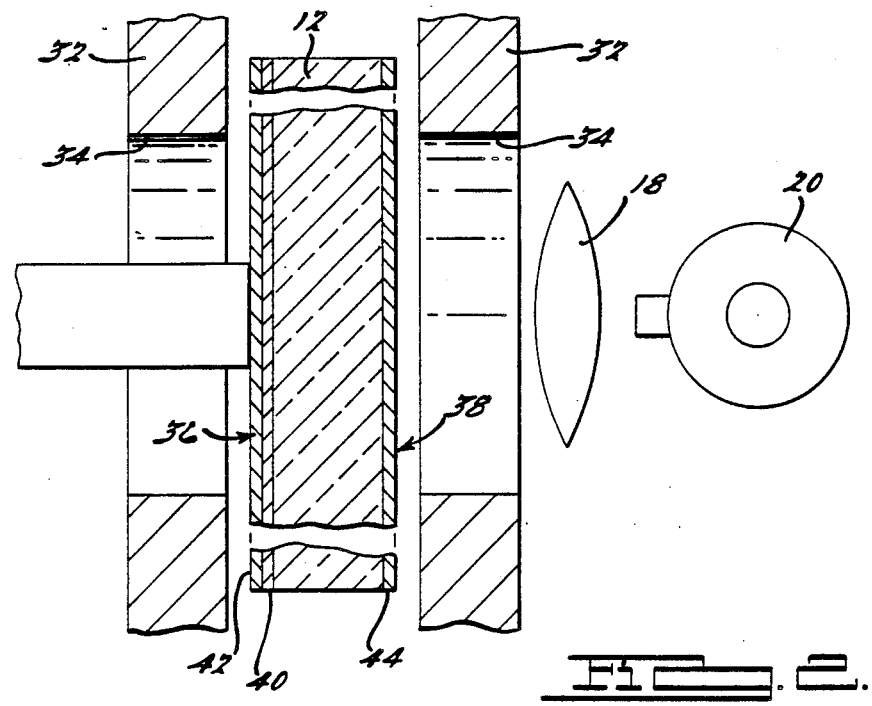
FIG. 2 is an enlarged cross-sectional view of an exemplary sample undergoing diffusivity measurement in accordance with the invention.
Figure 3:
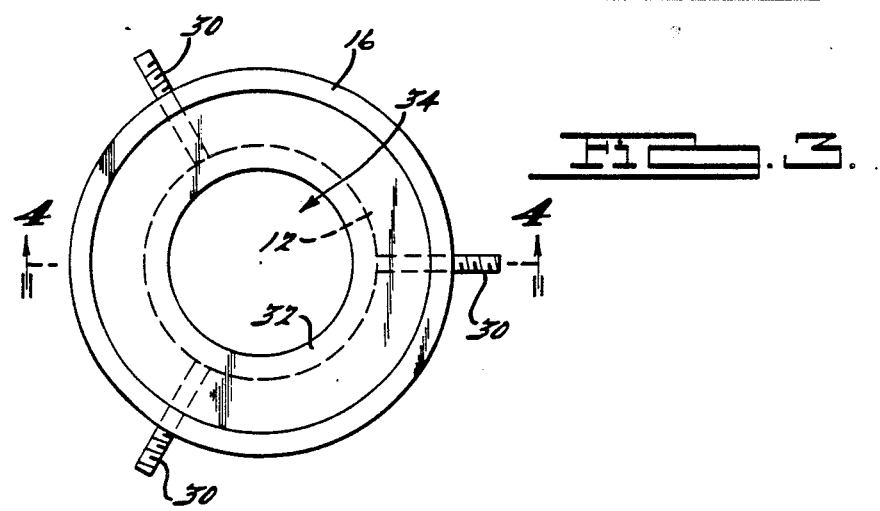
FIG. 3 is a plan view of a presently preferred sample holder useful in practicing the invention.
Figure 4:
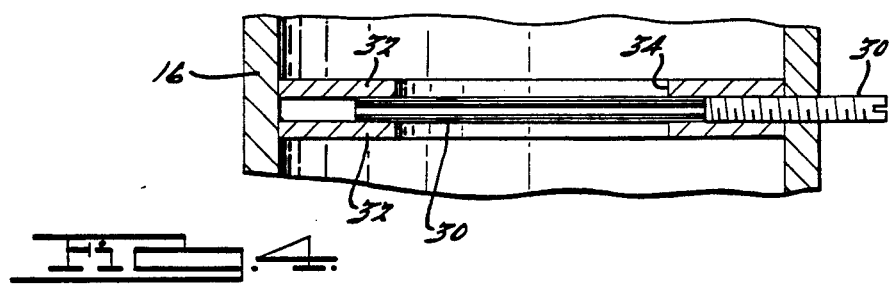
FIG. 4 is a cross-sectional view taken substantially along the line 4—4 of FIG. 3 illustrating the sample holder in greater detail.

With reference to FIGS. 2, 3 and 4, sample 12 is preferably held in holder 16 by means of three nylon set screws 30. The sample 12 is sufficiently thin to permit set screws 30 to act as spacers which prevent the annular graphite masks 32 from touching the sample Masks 32 have circular openings 34 through which the laser beam may illuminate the sample and through which blackbody emission from the sample may reach the detector 20.

If required, the sample can be provided with a suitable opaque coating to prevent the laser light and plasma generated at the first surface or portion 36 from reaching the sensor 20 positioned to monitor the second surface or portion 38. One presently preferred coating comprises a layer 40 of sputtered gold deposited on first surface or portion 36, followed by a layer of sputtered carbon 42. The second surface or portion 38 may also be provided with a coating such as a layer of sputtered carbon 44.

A 3 inch focal length CaF2 lens 18 collects and focuses the thermal radiation emitted from the second surface of sample 12 onto the input aperture of infrared detector 20. Detector 20 can be an InSb photovoltaic detector operating at 77° Kelvin. The infrared detector of the presently preferred embodiment has a peak sensitivity at a wavelength of 6 microns. The typical sample at room temperature may have a blackbody radiation energy distribution normally centered about a wavelength of approximately 10 microns. As the sample temperature increases in response to the applied thermal pulse, the blackbody radiant energy distribution of the sample shifts towards the shorter wavelengths. As this occurs, the infrared detector receives increasingly more signal at the 6 micron wavelength, thereby giving an indication of increased temperature. Of course, other types of sensors and sensors sensitive at other wavelengths can be used to suit the particular samples under test, temperatures and other test conditions. For example, a HgCdTe infrared detector can also be used.

The signal from detector 20 is amplified in matched preamplifier 22. The output of amplifier 22 is supplied to an analog processor 23 which further amplifies the signal. The output of processor 23 is supplied to a transient recorder 24 which includes analog-to-digital converters for digitizing the output signal. The transient recorder can be implemented using a Stanford Research Systems Model SR225.

To reduce the effect of AC noise on the signal developed by amplifier 22, the sample 12, detector 20, and preferably amplifier 22 can be enclosed in a metal box 26, which functions as a Faraday cage. The analog processor is configured to add the signals from the infrared detector and a battery power supply. By adjusting the voltage of the battery power supply the background voltage from the detector is nulled to give essentially a zero reading at the ambient sample temperature prior to subjecting the sample to a thermal pulse. In this regard, the sample can be maintained at ambient room temperature, or the cage can be placed in or configured to serve as a heating or cooling chamber, should it be desired to measure diffusivity at temperatures other than room temperature.

The transient recorder further includes a digital memory device which collects each digitized scan of thermal data and stores it in a two-state memory device such as random access memory for storing binary data.

The stored data from transient recorder 24 is transferred to a microcomputer terminal 26 which in turn communicates with a mainframe computer 28. The presently preferred embodiment uses a Digital Equipment Corporation LSI/11 microcomputer terminal connected to a VAX 11/785 mainframe computer.

In practicing the inventive method in accordance with the presently preferred embodiment microcomputer 26 triggers laser 10 causing a first radiant energy pulse to be applied to the first surface or portion 36 of sample 12. If laser 10 is in the Q-switched mode, the pulse is approximately 10 nanoseconds in duration. In the non-Q-switched mode, the pulse is approximately 120 milliseconds in duration. The Q-switched mode thus produces a larger radiant energy peak intensity than the non-Q-switched mode. For samples which require opaque coatings, the lower peak intensity non-Q-switched mode is preferred.

It has been found that opaque coatings can be damaged when subjected to thermal pulses of intensity above a certain level. It is believed that high intensity thermal pulses cause ablation, sublimation or other phase change in the coating as a consequence of rapid or excessive surface temperature rise. For a graphite film coating (dgf 123, Miracle Power Products, Inc., Cleveland, Ohio) it has been empirically determined that for a 10 nanosecond (nsec) pulse coating damage will occur at energy levels above about 0.040 joules, corresponding to a peak laser power exceeding 4 megawatts. More specifically, Table I sets forth the data from which this empirical determination has been made.

TABLE I

| Energy (mJ) | Peak Power (MW) | Damage (Y/N) |
| --- | --- | --- |
| 40 | 4 | N |
| 70 | 7 | Y |
| 90 | 9 | Y |
| 700 | 70 | Y |

Using the above data the front surface temperature can be calculated using the following equation where L is the thickness, $T_m$ is the maximum temperature, $\alpha$ is the diffusivity, y is the pulse width (10 nsec) and $\beta$ is a constant equal to approximately 2. (See Parker reference cited above.)

$$T_f = \frac{8LT_m}{3\beta(2\pi y)^{\frac{1}{2}}\alpha^{\frac{1}{2}}} \quad (5)$$

Assuming a diffusivity $\alpha$ of 1 cm$^2$/sec, which assumption implies a comparatively high thermal conductivity, and assuming the thickness L to be on the order of 0.2 cm and further assuming the maximum temperature $T_m$ to be 1° C., the maximum front surface temperature becomes approximately 550° C. for the graphite film (dgf 123). Of course, other coatings may have different maximum temperature ratings which can be empirically determined or estimated from the above data.

Having selected the proper laser power, microcomputer 26 pulses laser 10 on and off preferably at a rate of approximately 4–60 times per minute. The time between pulses should be sufficient to allow the thermal pulse to propagate through the sample from front surface or portion 36 to rear surface or portion 38 and to allow the sample to return to ambient temperature. For each pulse of radiant energy applied to the sample, the infrared detector collects the thermal response data at the second surface or portion 38 of sample 12 and provides a time varying analog signal to amplifier 22. If desired, the analog signal can be viewed on oscilliscope 50. However, it will be recalled that the laser power is comparatively low, and hence it can be expected that the analog signal will contain a substantial amount of random signal and noise.

The analog signal is amplified by amplifier 22 and normalized with respect to the ambient temperature by appropriate selection of the battery bias voltage applied to analog processor 23, so that the thermal response of the sample to the applied heat pulse can be measured relative to the ambient temperature baseline. The amplified data is digitized in the transient recorder into approximately 1000 data points in a time range from the laser pulse onset until the maximum temperature is reached on the order of three to four $t_{\frac{1}{2}}$ times thereafter.

After the digitized temperature data for a given individual pulse has been collected, the data is transferred to microcomputer 26 where the data is stored as individual temperature data points corresponding to each sample time. Thus if the analog data is sampled 1000 times, then 1000 data points are stored for a given thermal pulse. This process is then repeated for the desired number of scans, with the resulting digitized data being coadded to the previously stored data in microcomputer 26 for averaging or otherwise statistically manipulating to minimize the effects of random signals and noise. In the presently preferred embodiment the data collected from each pulse sequence is coadded and averaged sequentially with good results. Of course, other types of statistical processing could be practiced in place of or in addition to averaging if warranted by the particular nature of the desired signal vis-a-vis noise. Preferably greater than 100 scans are taken, with the data for each scan being stored and processed as described above.

When the desired number of scans has been completed and the data collected and statistically processed by averaging or the like, the data in microcomputer 26 is converted from a binary form to an ASCII form for transfer to the mainframe computer 28. The mainframe computer operates upon this data using a RS/E least squares curve fitting algorithm in order to fit the data to the analytical expression:

$$f(x) = c + b(1 - 2\exp(-ax) + 2\exp(-4ax)) \quad (3)$$

where (c) is the baseline of the curve, (b) is the amplitude of the curve and (a) is directly related to the diffusivity ($\alpha$) by the equation:

$$\alpha = a(L/\pi) \quad (4)$$

Suitable software for performing the least squares curve fit algorithm is available for the VAX 11/785 computer from BBN Software Products Corporation. The least squares fit algorithm performs a successive number of iterations by adjusting parameters a, b and c of equation (3) until the optimal fit is achieved. The diffusivity is then calculated using equation (4) and the result may be output for display on microcomputer terminal 26. The display may include the numerically calculated diffusivity value ($\alpha$) and may also include a graphical display of the data superimposed upon the curve determined by the curve fit algorithm. FIG. 5 illustrates an exemplary output curve including the actual data 60 and the superimposed curve fit data 70. As will be seen, the curve fit data matches the actual data quite closely.

Equation (3) comprises the first two terms of an infinite series:

$$\frac{T}{T_m} = 1 + 2 \sum_{n=1}^{\infty} - 1^n \exp(-n^2\pi^2\alpha t/L^2) \quad (6)$$

where $T_m$ is the maximum temperature, $\alpha$ is the diffusivity, n is the index, t is the time, L is the thickness and T is the temperature. If desired, a greater number or fewer number of terms of this series can be used, with the greater number providing greater accuracy and the lesser number providing a lesser accuracy. The number of terms selected for the curve fit computation is inversely related to the computation time required to find a suitable fit. Using only two terms of the series the present invention has demonstrated very good results with a resolution on the order of 1/10th of a degree Centigrade.

While it will be apparent that the invention herein described is well calculated to achieve the benefits and advantages as hereinabove set forth, it will be appreciated that the invention is susceptible to modification, variation and change without departing from the spirit thereof.

We claim:

1. A method of ascertaining the thermal diffusivity of a sample comprising:

applying a plurality of discrete temporally-spaced radiant energy pulses to a first portion of said sample, each of said radiant energy pulses having a peak power below the level at which damage to said sample occurs, each of said radiant energy pulses causing a discrete temperature rise pulse to propagate through said sample to a second portion of said sample;

sensing said temperature rise pulses at said second portion and electrically recording said sensed temperature rise pulses as data in a two-state memory device wherein each discrete temperature rise pulse corresponds to a discrete datum;

statistically processing said data to derive a set of favored values indicative of the temperature of said second portion as a function of time; and further processing said set of favored values to determined the thermal diffusivity of said sample.

2. The method of claim 1 wherein said step of statistically processing said data comprises averaging said data.

3. The method of claim 1 wherein said step of further processing said set of favored values comprises operating on said favored values using a least squares curve fitting algorithm.

4. The method of claim 3 wherein said curve fitting algorithm is selected to fit said set of favored values to the following equation:

$$f(x) = c + b(1 - 2\exp(-ax) + 2\exp(-4ax))$$

where c is the baseline of a curve defined by said set of favored values, wherein b is the amplitude of said curve and wherein a is related to the thermal diffusivity of said sample.

5. The method of claim 3 wherein said curve fitting algorithm is selected to fit said set of favored values to the following equation:

$$\frac{T}{T_m} = 1 + 2 \sum_{n=1}^{\infty} - 1^n \exp(-n^2\pi^2\alpha t/L^2)$$

where $T_m$ is the maximum temperature, $\alpha$ is the diffusivity, n is the index, t is the time, L is the thickness and T is the temperature.

6. The method of claim 1 wherein said radiant energy pulses have a peak power below one joule.

7. The method of claim 1 further comprising applying an opaque coating to said sample prior to said step of applying a plurality of temporally-spaced radiant energy pulses and wherein said radiant energy pulses have a peak power below the level at which damage to said coating occurs.

8. An apparatus for ascertaining the thermal diffusivity of a sample comprising:

a support stand;

a laser means disposed on said support stand for applying a plurality of discrete temporally-spaced radiant energy pulses to a first portion of said sample, each of said pulses having a peak power below the level at which damage to said sample occurs, each of said pulses causing a discrete temperature rise pulse to propagate through said sample to a second portion of said sample;

a means for sensing said temperature rise pulses at said second portion disposed on said support stand;

a means coupled to said sensing means for electrically recording each of said sensed temperature rise pulses as data in a two-state memory device wherein each discrete temperature rise pulse corresponds to a discrete datum;

means coupled to said recording means for statistically processing said data to derive a set of favored values indicative of the temperature of said second portion as a function of time and for further processing said set of favored values to determined the diffusivity of said sample.

* * * * *